United States Patent
De La Cruz

(10) Patent No.: US 11,913,082 B2
(45) Date of Patent: *Feb. 27, 2024

(54) COMPOSITIONS AND METHODS FOR USE IN A PCR ASSAY FOR DETERMINING THE GENOTYPE AND VIRAL LOAD FOR RESPIRATORY SYNCYTIAL VIRUS

(71) Applicant: Laboratory Corporation of America Holdings, Burlington, NC (US)

(72) Inventor: Justin Philip De La Cruz, Mountain View, CA (US)

(73) Assignee: Laboratory Corporation of America Holdings, Burlington, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/908,020

(22) Filed: Jun. 22, 2020

(65) Prior Publication Data
US 2021/0180143 A1 Jun. 17, 2021

Related U.S. Application Data

(63) Continuation of application No. 15/242,856, filed on Aug. 22, 2016, now Pat. No. 10,689,715.

(60) Provisional application No. 62/244,320, filed on Oct. 21, 2015, provisional application No. 62/208,556, filed on Aug. 21, 2015.

(51) Int. Cl.
*C12Q 1/70* (2006.01)

(52) U.S. Cl.
CPC ....... *C12Q 1/701* (2013.01); *C12Q 2600/156* (2013.01); *C12Q 2600/158* (2013.01); *C12Q 2600/16* (2013.01)

(58) Field of Classification Search
CPC .............. C12Q 1/701; C12Q 2600/156; C12Q 2600/158; C12Q 2600/16
See application file for complete search history.

(56) References Cited

U.S. PATENT DOCUMENTS

| | | | |
|---|---|---|---|
| 6,841,346 B1 | 1/2005 | O'Connell et al. | |
| 10,689,715 B2 * | 6/2020 | De La Cruz | C12Q 1/701 |
| 2007/0065813 A1 * | 3/2007 | Hayden | C12Q 1/701 |
| | | | 435/5 |
| 2012/0308602 A1 * | 12/2012 | Jin | C12N 7/00 |
| | | | 435/236 |
| 2017/0051363 A1 | 2/2017 | De La Cruz | |

FOREIGN PATENT DOCUMENTS

| | | |
|---|---|---|
| WO | 2009/009900 A1 | 1/2009 |
| WO | 2013/128405 A1 | 9/2013 |
| WO | 2017/035049 A1 | 3/2017 |

OTHER PUBLICATIONS

Perkins., Journal of Clinal Microbiology, vol. 43, No. 5, pp. 2356-2362, May (Year: 2005).*

Collins, P et al., "The Two Open Reading Frames of the 22K mRNA of Human Respiratory Syncytial Virus: Sequence Comparison of Antigenic Subgroups A and B and Expression in vitro," J. General Virology 71(12):3015-3020 (1990).

Database Geneseq, Database accession No. ADW28366, "Bacteriophage MS2 target DNA specific PCR probe 1," Mar. 24, 2005.

Database Geneseq retrieved from EBI accession No. GSN:AAI66211, "Respiratory syncytial virus NS1 and NS2 genes PCR primer Nstu(-)," Jan. 15, 2002.

Dewhurst-Maridor, G. et al., "Development of a Quantitative TaqMan RT-PCR for Respiratory Syncytial Virus," J. Virol. Methods 120(1):41-49 (2004).

Ha Do, L. et al., "A Sensitive Real-Time PCR for Detection and Subgrouping of Human Respiratory Syncytial Virus," J. Virol. Methods 179(1):250-255 (2012).

Douglas, J. et al., "Small Molecules VP-14637 and JNJ-2408068 Inhibit Respiratory Syncytial Virus fusion by Similar Mechanisms," Antimicrob. Agents Chemother. 49(6):2460-2466 (2005).

Jordan, R. et al., "Antiviral Efficacy of a Respiratory Syncytial Virus (RSV) Fusion Inhibitor in a Bovine Model of RSV Infection," Antimicrob. Agents Chemother. 59:4889-4900 (2015).

Kuypers, J. et al., "Evaluation of Quantitative and Type-Specific Real-Time RT-PCR Assays for Detection of Respiratory Syncytial Virus in Respiratory Specimens from Children," J. Clin. Virol. 31(2):123-129 (2004).

Landolt, G. et al., "Use of real-time reverse transcriptase polymerase chain reaction assay and cell culture methods for detection of swine influenza A viruses," Am. J. Vet. Res. 66:119-124 (2005).

Perkins, S. et al., "Comparison of a Real-Time Reverse Transcriptase PCR Assay and a Culture Technique for Quantitative Assessment of Viral Load in Children Naturally Infected with Respiratory Syncytial Virus," J. Clin. Microbiol. 43(5):2356-2362 (2005).

Payungporn, S. et al. "Single step multiplex real-time RT-PCR for H5N 1 influenza A virus detection," J. Virol Methods 131:143-147 (2006).

Van Elden, L. et al., "Applicability of a Real-Time Quantitative PCR Assay for Diagnosis of Respiratory Syncytial Virus Infection in Immunocompromised Adults," J. Clin. Microbiol. 41(9):4378-4381 (2003).

(Continued)

*Primary Examiner* — Cynthia B Wilder
(74) *Attorney, Agent, or Firm* — Kilpatrick Townsend & Stockton LLP

(57) ABSTRACT

Methods are provided for a sensitive and specific assay for the determination of viral load and genotyping of RSV in a biological sample. Compositions and kits for use in the methods also are provided, including optimized primers for the amplification of and detection of the RSV open reading frames from subtypes A and B, and probes for distinguishing between the subtypes. Also provided are methods for amplifying and sequencing an open reading from of an RSV F protein, and compositions and kits for use in the methods.

15 Claims, 7 Drawing Sheets

Specification includes a Sequence Listing.

(56) References Cited

OTHER PUBLICATIONS

U.S. Appl. No. 15/242,856, Corrected Notice of Allowability, dated Apr. 2, 2020, 4 pages.
U.S. Appl. No. 15/242,856, Final Office Action, dated Jul. 16, 2019, 11 pages.
U.S. Appl. No. 15/242,856, Non-Final Office Action, dated Nov. 13, 2018, 11 pages.
U.S. Appl. No. 15/242,856, Notice of Allowance, dated Feb. 10, 2020, 12 pages.
PCT/US2016/047962, International Preliminary Report on Patentability, dated Mar. 8, 2018, 7 pages.
PCT/US2016/047962, International Search Report and Written Opinion, dated Feb. 1, 2017, 24 pages.
PCT/US2016/047962, Invitation to Pay Additional Fees and Partial Search Report, dated Dec. 5, 2016, 9 pages.

\* cited by examiner

FIGURE 1A
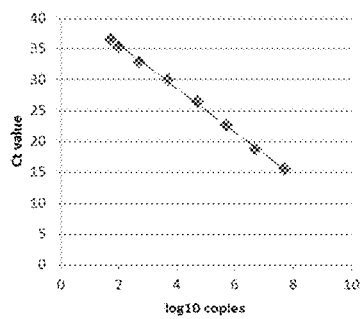
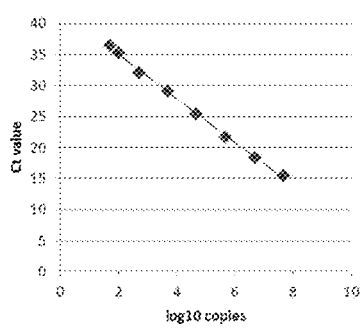
FIGURE 1B
| Input | | | Measured | |
|---|---|---|---|---|
| copies | log10 copies | RSVA Ct | log10 copies | copies |
| 5.00E+07 | 7.70 | 15.54 | 7.69 | 48,769,747 |
| 5.00E+06 | 6.70 | 18.64 | 6.81 | 6,421,794 |
| 5.00E+05 | 5.70 | 22.53 | 5.70 | 503,450 |
| 5.00E+04 | 4.70 | 26.44 | 4.59 | 39,169 |
| 5.00E+03 | 3.70 | 30.03 | 3.57 | 3,748 |
| 5.00E+02 | 2.70 | 32.89 | 2.76 | 575 |
| 1.00E+02 | 2.00 | 35.33 | 2.07 | 117 |
| 5.00E+01 | 1.70 | 36.62 | 1.70 | 50 |
| Input | | | Measured | |
|---|---|---|---|---|
| copies | log10 copies | RSVB Ct | log10 copies | copies |
| 5.00E+07 | 7.70 | 15.39 | 7.57 | 37,163,632 |
| 5.00E+06 | 6.70 | 18.24 | 6.76 | 5,782,907 |
| 5.00E+05 | 5.70 | 21.72 | 5.78 | 595,884 |
| 5.00E+04 | 4.70 | 25.48 | 4.71 | 51,425 |
| 5.00E+03 | 3.70 | 29.05 | 3.70 | 5,000 |
| 5.00E+02 | 2.70 | 32.10 | 2.83 | 681 |
| 1.00E+02 | 2.00 | 35.27 | 1.94 | 87 |
| 5.00E+01 | 1.70 | 36.44 | 1.60 | 40 |
Range = 50 – 5x10$^7$ copies

| Controls | Multiplex qRT-PCR | |
|---|---|---|
|  | RSVA | RSVB |
| PC1_A | 21.92 | UND |
| PC2_A | 21.55 | UND |
| NTC | UND | UND |
| NTC | UND | UND |
| PC1_B | UND | 20.57 |
| PC2_B | UND | 20.54 |

NTC = no template control
UND = undetermined
PC = positive control

| LabCorp_RSV | Multiplex qRT-PCR | | GenMark RVP | |
|---|---|---|---|---|
|  | RSVA | RSVB | RSVA | RSVB |
| 2015-1 | 26.12 | UND | X |  |
| 2015-2 | 27.03 | UND | X |  |
| 2015-3 | UND | 28.23 |  | X |
| 2015-4 | UND | 28.10 |  | X |
| 2015-5 | 29.17 | UND | X |  |
| 2015-6 | UND | 31.11 |  | X |
| 2015-7 | UND | 29.76 |  | X |
| 2015-8 | UND | 28.94 |  | X |
| 2015-9 | UND | 29.13 |  | X |
| 2015-10 | UND | 26.19 |  | X |

All qRT-PCR reactions performed in triplex

| LabCorp_RSV | Multiplex qRT-PCR | | GenMark RVP | |
|---|---|---|---|---|
|  | RSVA | RSVB | RSVA | RSVB |
| 2014-1 | UND | 25.59 |  | X |
| 2014-2 | UND | 27.35 |  | X |
| 2014-3 | UND | 27.28 |  | X |
| 2014-4 | UND | 28.17 |  | X |
| 2014-5 | UND | 37.70 |  | X |
| 2014-6 | 27.48 | UND | X |  |
| 2014-7 | UND | 31.76 |  | X |
| 2014-8 | UND | 29.35 |  | X |
| 2014-9 | 25.65 | UND | X |  |
| 2014-10 | 31.93 | UND | X |  |
| 2014-11 | UND | 23.85 |  | X |
| 2014-12 | UND | 27.49 |  | X |
| 2014-13 | 30.10 | UND | X |  |
| 2014-14 | 27.48 | UND | X |  |
| 2014-15 | UND | 26.77 |  | X |
| 2014-16 | 30.97 | UND | X |  |
| 2014-17 | 26.02 | UND | X |  |
| 2014-18 | 27.23 | UND | X |  |
| 2014-19 | UND | 30.63 |  | X |
| 2014-20 | 26.45 | UND | undetected by RVP | |

|  | | Known VL | MGB 3plex |  | | Known VL | MGB 3plex |
|---|---|---|---|---|---|---|---|
| RSV A | 1A.1 | 1,100,000 | 2,249,378 | RSV B | 2A.1 | 44,000,000 | 30,513,179 |
| | 1A.2 | 1,300,000 | 2,172,043 | | 2A.2 | 24,000,000 | 21,187,163 |
| | 1A.3 | 1,200,000 | 2,227,539 | | 2A.3 | 26,000,000 | 25,762,193 |
| | 1B.1 | 893,000 | 256,557 | | 2B.1 | 2,100,000 | 3,414,058 |
| | 1B.2 | 136,000 | 265,169 | | 2B.2 | 1,400,000 | 2,360,924 |
| | 1B.3 | 120,000 | 210,356 | | 2B.3 | 2,900,000 | 2,426,159 |
| | 1C.1 | 12,600 | 27,987 | | 2C.1 | 134,000 | 120,437 |
| | 1C.2 | 14,200 | 36,763 | | 2C.2 | 67,600 | 100,514 |
| | 1C.3 | 13,100 | 27,952 | | 2C.3 | 229,000 | 176,436 |
| | 1D.1 | 1,960 | 3,437 | | 2D.1 | 12,200 | 4,886 |
| | 1D.2 | 2,350 | 3,240 | | 2D.2 | 45,900 | 9,821 |
| | 1D.3 | 1,650 | 4,506 | | 2D.3 | 5,800 | 10,809 |
| | 1E.1 | 140 | 445 | | 2E.1 | 500 | 116 |
| | 1E.2 | ND | 2,196 | | 2E.2 | 800 | 814 |
| | 1E.3 | 1,530 | 998 | | 2E.3 | 700 | 206 |

FIGURE 5

FIGURE 7A
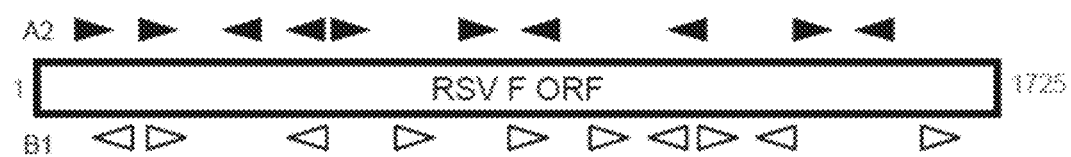
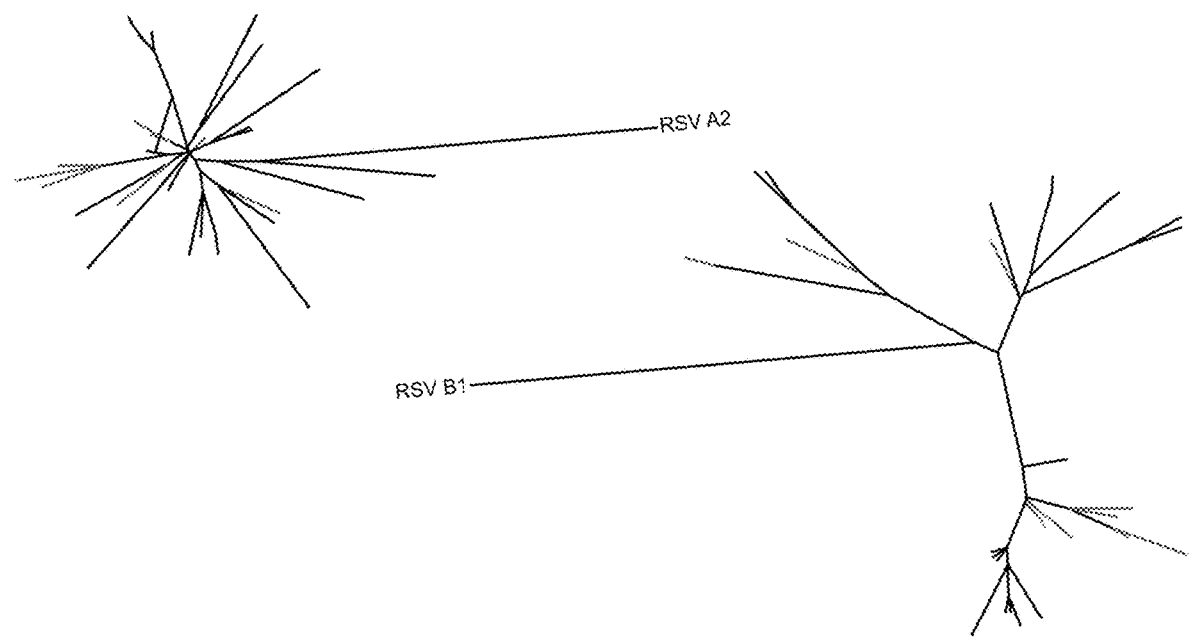
FIGURE 7B

SEQUENCE LISTING

<160> NUMBER OF SEQ ID NOS: 37

<210> SEQ ID NO 1
<211> LENGTH: 20
<212> TYPE: DNA
<213> ORGANISM: Artificial sequence
<220> FEATURE:
<223> OTHER INFORMATION: Synthetic construct

<400> SEQUENCE: 1
gtvataacca aattagcagc					20

<210> SEQ ID NO 2
<211> LENGTH: 21
<212> TYPE: DNA
<213> ORGANISM: Artificial sequence
<220> FEATURE:
<223> OTHER INFORMATION: Synthetic construct

<400> SEQUENCE: 2
cacttcatar aarctgttdg c					21

<210> SEQ ID NO 3
<211> LENGTH: 26
<212> TYPE: DNA
<213> ORGANISM: Artificial sequence
<220> FEATURE:
<223> OTHER INFORMATION: Synthetic construct

<400> SEQUENCE: 3
tgaaatgaaa cgttataaag gcttac				26

<210> SEQ ID NO 4
<211> LENGTH: 26
<212> TYPE: DNA
<213> ORGANISM: Artificial sequence
<220> FEATURE:
<223> OTHER INFORMATION: Synthetic construct

<400> SEQUENCE: 4
cgaaataaaa cghtacaagg gcctva				26

<210> SEQ ID NO 5
<211> LENGTH: 26
<212> TYPE: DNA
<213> ORGANISM: Artificial sequence
<220> FEATURE:
<223> OTHER INFORMATION: Synthetic construct

<400> SEQUENCE: 5
taaggcccaa atctcagcca tgcatc				26

<210> SEQ ID NO 6
<211> LENGTH: 35
<212> TYPE: DNA
<213> ORGANISM: Artificial sequence
<220> FEATURE:
<223> OTHER INFORMATION: Synthetic construct

<400> SEQUENCE: 6
gggctcgaga ccggttctgg ggcaaataac aatgg			35

<210> SEQ ID NO 7
<211> LENGTH: 39
<212> TYPE: DNA
<213> ORGANISM: Artificial sequence
<220> FEATURE:
<223> OTHER INFORMATION: Synthetic construct

<400> SEQUENCE: 7
gggtctagaa cgcgttaggt gctattttta tttagttac                39

<210> SEQ ID NO 8
<211> LENGTH: 35
<212> TYPE: DNA
<213> ORGANISM: Artificial sequence
<220> FEATURE:
<223> OTHER INFORMATION: Synthetic construct

<400> SEQUENCE: 8
gggctcgaga ccggtcctgg ggcaaataac catgg                    35

<210> SEQ ID NO 9
<211> LENGTH: 39
<212> TYPE: DNA
<213> ORGANISM: Artificial sequence
<220> FEATURE:
<223> OTHER INFORMATION: SEQ ID NO: 10

<400> SEQUENCE: 9
gggtctagaa cgcgttcagg tggttttttg tctatttgc                39

<210> SEQ ID NO 10
<211> LENGTH: 26
<212> TYPE: DNA
<213> ORGANISM: Artificial sequence
<220> FEATURE:
<223> OTHER INFORMATION: Synthetic construct

<400> SEQUENCE: 10
ctctggggca ataacaatg gagttg                               26

<210> SEQ ID NO 11
<211> LENGTH: 27
<212> TYPE: DNA
<213> ORGANISM: Artificial sequence
<220> FEATURE:
<223> OTHER INFORMATION: Synthetic construct

<400> SEQUENCE: 11
gtcaaaacat cactgaagaa ttttatc                             27

<210> SEQ ID NO 12
<211> LENGTH: 25
<212> TYPE: DNA
<213> ORGANISM: Artificial sequence
<220> FEATURE:
<223> OTHER INFORMATION: Synthetic construct

<400> SEQUENCE: 12
cttcttttcc ttttcttgct taatg                               25

<210> SEQ ID NO 13
<211> LENGTH: 25
<212> TYPE: DNA
<213> ORGANISM: Artificial sequence
<220> FEATURE:
<223> OTHER INFORMATION: Synthetic construct

<400> SEQUENCE: 13
ctggcgattg cagatccaac accta                               25

<210> SEQ ID NO 14
<211> LENGTH: 30
<212> TYPE: DNA
<213> ORGANISM: Artificial squence
<220> FEATURE:
<223> OTHER INFORMATION: synthetic construct

<400> SEQUENCE: 14
gctctactat ccacaaacaa ggctgtagtc                               30

<210> SEQ ID NO 15
<211> LENGTH: 25
<212> TYPE: DNA
<213> ORGANISM: Artificial sequence
<220> FEATURE:
<223> OTHER INFORMATION: Synthetic construct

<400> SEQUENCE: 15
gcctataaca aatgatcaga aaaag                                    25

<210> SEQ ID NO 16
<211> LENGTH: 28
<212> TYPE: DNA
<213> ORGANISM: Artificial sequence
<220> FEATURE:
<223> OTHER INFORMATION: Synthetic construct

<400> SEQUENCE: 16
catgatagag taactttgct gtctaact                                 28

<210> SEQ ID NO 17
<211> LENGTH: 26
<212> TYPE: DNA
<213> ORGANISM: Artificial sequence
<220> FEATURE:
<223> OTHER INFORMATION: Synthetic construct

<400> SEQUENCE: 17
gatcctgcat tgtcacagta ccatcc                                   26

<210> SEQ ID NO 18
<211> LENGTH: 25
<212> TYPE: DNA
<213> ORGANISM: Artificial sequence
<220> FEATURE:
<223> OTHER INFORMATION: Synthetic construct

<400> SEQUENCE: 18
gagatattga tgcatcaaat tcatc                                    25

<210> SEQ ID NO 19
<211> LENGTH: 26
<212> TYPE: DNA
<213> ORGANISM: Artificial sequence
<220> FEATURE:
<223> OTHER INFORMATION: Synthetic construct

<400> SEQUENCE: 19
gtctctatgt aaaaggtgaa ccaata                                   26

<210> SEQ ID NO 20
<211> LENGTH: 25
<212> TYPE: DNA
<213> ORGANISM: Artificial sequence
<220> FEATURE:
<223> OTHER INFORMATION: Synthetic construct

<400> SEQUENCE: 20
gattgcactt gatctatgga tcagc                                          25

<210> SEQ ID NO 21
<211> LENGTH: 27
<212> TYPE: DNA
<213> ORGANISM: Artificial sequence
<220> FEATURE:
<223> OTHER INFORMATION: Synthetic construct

<400> SEQUENCE: 21
gtcagaacat aactgaggag ttttacc                                        27

<210> SEQ ID NO 22
<211> LENGTH: 27
<212> TYPE: DNA
<213> ORGANISM: Artificial sequence
<220> FEATURE:
<223> OTHER INFORMATION: Synthetic construct

<400> SEQUENCE: 22
cttcaaggtg tagaactttg gatacag                                        27

<210> SEQ ID NO 23
<211> LENGTH: 27
<212> TYPE: DNA
<213> ORGANISM: Artificial sequence
<220> FEATURE:
<223> OTHER INFORMATION: Synthetic construct

<400> SEQUENCE: 23
gaattccagc agaagaacag cagattg                                        27

<210> SEQ ID NO 24
<211> LENGTH: 20
<212> TYPE: DNA
<213> ORGANISM: Artificial sequence
<220> FEATURE:
<223> OTHER INFORMATION: Synthetic construct

<400> SEQUENCE: 24
cagatagtaa ggcaacaaag                                                20

<210> SEQ ID NO 25
<211> LENGTH: 20
<212> TYPE: DNA
<213> ORGANISM: Artificial sequence
<220> FEATURE:
<223> OTHER INFORMATION: Synthetic construct

<400> SEQUENCE: 25
gtacagctac ctatctatgg                                                20

<210> SEQ ID NO 26
<211> LENGTH: 22
<212> TYPE: DNA
<213> ORGANISM: Artificial sequence
<220> FEATURE:
<223> OTHER INFORMATION: Synthetic construct

<400> SEQUENCE: 26
gtcacaaaat actcgattgg ac                                             22

<210> SEQ ID NO 27

```
<210> SEQ ID NO 27
<211> LENGTH: 24
<212> TYPE: DNA
<213> ORGANISM: Artificial sequence
<220> FEATURE:
<223> OTHER INFORMATION: Synthetic construct

<400> SEQUENCE: 27
catacttgga attgaatatg tcag                                          24

<210> SEQ ID NO 28
<211> LENGTH: 25
<212> TYPE: DNA
<213> ORGANISM: Artificial sequence
<220> FEATURE:
<223> OTHER INFORMATION: Synthetic construct

<400> SEQUENCE: 28
cattaccaag tgaagtcagc ctttg                                         25

<210> SEQ ID NO 29
<211> LENGTH: 25
<212> TYPE: DNA
<213> ORGANISM: Artificial sequence
<220> FEATURE:
<223> OTHER INFORMATION: Synthetic construct

<400> SEQUENCE: 29
gtgtcaaaca aaggagtaga tactg                                         25

<210> SEQ ID NO 30
<211> LENGTH: 20
<212> TYPE: DNA
<213> ORGANISM: Artificial sequence
<220> FEATURE:
<223> OTHER INFORMATION: Synthetic construct

<400> SEQUENCE: 30
tgtggagaga cagggcactg                                               20

<210> SEQ ID NO 31
<211> LENGTH: 21
<212> TYPE: DNA
<213> ORGANISM: Artificial sequence
<220> FEATURE:
<223> OTHER INFORMATION: Synthetic construct

<400> SEQUENCE: 31
cagttgttgg ccatacggat t                                             21

<210> SEQ ID NO 32
<211> LENGTH: 1175
<212> TYPE: DNA
<213> ORGANISM: Artificial sequence
<220> FEATURE:
<223> OTHER INFORMATION: Synthetic construct

<400> SEQUENCE: 32
atggctctta gcaaagtcaa gttgaaygat acactcaaca agatcaact tctgtcatcc    60 agcaaataca ccatccaacg gagcacagga gayagyattg ayactcctaa ttatgatgtg   120
cagaaacaca tcaayaagyt atgtggcatg ttattaatca cagaagatgc taatcataaa   180
ttcactgggk taataggtat gttatatgct atgtctagat taggaagaga agacaccata   240
aaaatactca ragatgcdgg atatcatgta aaagcwaatg gagtggatgt aacaacacat   300
cgtcaagaya ttaatggraa agaaatgaaa tttgaagtgt taacattrgc aagcttaaca   360
```

```
actgaaattc aaatcaacat tgagatagaa tctagraaat cctacaaaaa aatgctaaaa      420
gaaatgggag aggtrgctcc agaatacagg catgactcwc ctgattgtgg ratgataata      480
ttatgtatag crgcattagt aataaccaaa ttagcagcag gggatagatc tggtcttaca      540
gcygtratta ggagagctaa taatgtycta aaaaatgaaa tgaacgtta taaaggctta       600 ctacchaagg atatagchaa cagyttctat gaagtgtttg aaaaatatcc tcactttata      660 gatgttttg ttcattttgg tatagcacaa tcttctacca gaggtggcag tagagttgaa       720 gggattttg caggattgtt tatgaatgcc tatggtgcag ggcaagtgat gttacggtgg       780
grgtcttagc aaaatcagtt aaaaatatta tgytaggaca cgctagtgtg caagcagaaa      840
tggaacaagt tgtggargtd tatgaatatg cccaaaaatt gggtggagaa gcaggattct      900
accatatatt gaayaaccca aaagcatcat tattatcttt gactcaatty ccycacttct      960
cyagtgtagt attrggcaat gctgctggcc taggcataat gggagaatac agaggtacac     1020
caaggaatca agatctatat gatgctgcda argcatatgc tgaacaactc aaagaaaatg     1080
gtgtgattaa ctacagtgta ttagacttga cagcagaaga actagaggct atcaaacatc     1140
agcttaatcc aaaagataat gatgtagagc tttga                                1175

<210> SEQ ID NO 33
<211> LENGTH: 1176
<212> TYPE: DNA
<213> ORGANISM: Artificial sequence
<220> FEATURE:
<223> OTHER INFORMATION: Synthetic construct

<400> SEQUENCE: 33
atggctctta gcaaagtcaa gttraatgat acattaaata aggatcagct gctgtcatcc       60
agcaaataca ctattcaacg tagtacagga gataatattg acactcccaa ttatgatgtr      120
caaaaacacy taaacaaact atgtggtatg ctattaatca ctgaagatgc aaatcataaa      180
ttcacaggat taataggtat gytatatgct atgtccaggt taggaaggga agacactata      240
aagatactta agatgctgg atatcatgtt aaagctaatg gagtagatat aacaacatat       300
cgtcaagata taaatggaaa ggaaatgaaa ttcgaagtat taacattatc aagcttgaca      360
tcagaaatac aagtcaatat tgagatagaa tctagaaagt cctacaaaaa aatgctaaaa      420
garatgggag aagtggctcc agaatatagg catgaytctc cagactgtgg gatgataata      480
ctrtgtatag cwgchcttgt vataaccaaa ttagcagcag gagayagatc aggtctyaca      540
gcagtaatta ggagrgcraa caatgtctta aaaaacgaaa taaacghta caagggcctv       600 ataccaaagg ayatagcyaa cagttttat gaagtgtttg aaaaacaccc tcatcttata      660
gatgttttyg tgcactttgg cattgcacaa tcatccacaa gaggggtag tagagttgaa      720 ggaatctttg caggattrtt tatgaatgcc tatggttcag grcaagtaat gctaagatgg      780
ggagttttag ccaaatctgt aaaaaatatc atgctaggwc atgctagtgt ccargcagaa      840
atggagcaag ttgtdgaagt ctatgagtat gcacagaagt tgggrggaga agctggwttc     900
taccatatat tgaacaatcc aaaagcatca ttgctgtcat taactcaatt tccyaacttc     960
tcaagtgtgg tcctaggcaa tgcagcaggy ctaggcataa tgggagagta tagaggtaca    1020
ccaagaaacc argatctyta tgatgcwgcc aaagcatatg cagagcaact caaagaaaat    1080
ggagtaataa actacagtgt attagactta acarcagaag aattggaagc cataaagmat    1140
caactcaacc ccaaagaaga tgaygtagag ctytaa                               1176
```

```
<210> SEQ ID NO 34
<211> LENGTH: 24
<212> TYPE: DNA
<213> ORGANISM: Artificial sequence
<220> FEATURE:
<223> OTHER INFORMATION: Synthetic construct

<400> SEQUENCE: 34
rgaaatgaaa ttygaagtrt taac                                    24

<210> SEQ ID NO 35
<211> LENGTH: 23
<212> TYPE: DNA
<213> ORGANISM: Artificial sequence
<220> FEATURE:
<223> OTHER INFORMATION: Synthetic construct

<400> SEQUENCE: 35
gartcatgcc trtattctgg agc                                     23

<210> SEQ ID NO 36
<211> LENGTH: 30
<212> TYPE: DNA
<213> ORGANISM: Artificial sequence
<220> FEATURE:
<223> OTHER INFORMATION: Synthetic construct

<400> SEQUENCE: 36
gcaagcttaa caactgaaat tcaaatcaac                              30

<210> SEQ ID NO 37
<211> LENGTH: 30
<212> TYPE: DNA
<213> ORGANISM: Artificial sequence
<220> FEATURE:
<223> OTHER INFORMATION: Synthetic construct

<400> SEQUENCE: 37
tcaagcttga catcagaaat acaagtcaat                              30
```

COMPOSITIONS AND METHODS FOR USE IN A PCR ASSAY FOR DETERMINING THE GENOTYPE AND VIRAL LOAD FOR RESPIRATORY SYNCYTIAL VIRUS

CROSS REFERENCE TO RELATED APPLICATIONS

This application claims priority to U.S. application Ser. No. 15/242,856, filed Aug. 22, 2016 (U.S. Pat. No. 10,689, 715), which claims priority to U.S. Provisional Application No. 62/208,556, filed Aug. 21, 2015 and U.S. Provisional Application No. 62/244,320, filed Oct. 21, 2015. The entire contents of each of these applications are incorporated herein by reference.

FIELD OF THE INVENTION

Embodiments of the present invention relate to the analysis of a respiratory syncytial virus ("RSV"). In particular, compositions and methods are provided for determining the genotype and/or viral load for RSV in a biological sample. Compositions and methods for sequencing a RSV fusion protein (F) are also provided.

BACKGROUND

RSV is a negative-sense, single-stranded RNA virus of the paramyxovirus family. RSV can cause severe respiratory infections in humans, particularly in infants and children, as well as in the elderly and immunocompromised. The RSV genome encodes the synthesis of several viral proteins, including three transmembrane glycoproteins (attachment glycoprotein (G), fusion protein (F), and small hydrophobic protein (SH)); matrix protein M; transcription antitermination protein (M2-1); regulatory protein (M2-2); three proteins associated with the nucleocapsid (N, P, and L); and two nonstructural proteins (NS1 and NS2). RSV strains may be separated into two main groups, genotypes A and B (RSV A and RSV B).

Human RSV (hRSV) is the major cause of severe respiratory infections such as bronchiolitis and lower tract illness affecting mostly newborns and young children. Approximately 30 million children younger than five years old suffer from acute lower respiratory infection due to hRSV, and hRSV causes numerous complications in premature born patients as well as infants suffering from congenital heart disease and immune deficiency. Long-term effects of RSV infection include central nervous system alterations, seizures, central apnea, and encephalopathy, to name a few. Over 200,000 deaths per year can be attributed to hRSV and there are no efficient therapies to counteract the disease. Therefore, efforts are focused on generating a vaccine to prevent hRSV infection as well as developing new therapeutic drugs to treat RSV infection and reduce the potential long-term effects caused by RSV infection.

In order for health care providers to determine the effectiveness of treatment for a particular individual or to determine the best course of treatment for a particular individual, it is important to determine the amount of RSV present in the individual and/or the genotype of RSV that has infected the individual. What is needed, therefore, are compositions and methods for the efficient genotyping of an RSV and for the efficient determination of viral load.

SUMMARY

Provided herein are methods for simultaneously determining the viral load and genotype of a respiratory syncytial virus (RSV) in a biological sample. These methods may include the steps of a) amplifying a nucleic acid sequence encoding an RSV open reading frame (ORF) in a biological sample using a set of primers that specifically amplifies an RSV subtype A ORF and/or an RSV subtype B ORF and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled; and b) determining the viral load and the RSV subtype(s) present in the biological sample.

Methods are provided for determining the genotype or viral load of a respiratory syncytial virus (RSV) in a biological sample. The methods may include the steps of a) amplifying a nucleic acid sequence encoding an RSV open reading frame (ORF) in a biological sample using a primer that comprises SEQ ID NO:1, a primer that comprises SEQ ID NO:2, a probe that comprises SEQ ID NO:3, and a probe that comprises SEQ ID NO:4 in a quantitative polymerase chain reaction assay, wherein the probes are differentially labeled; and b) determining the presence or absence of an amplification product that binds one of the probes, or determining the viral load, thereby determining the RSV genotype(s) present and/or viral load of the RSV in the biological sample. In addition, methods are provided for determining the genotype or viral load of a respiratory syncytial virus (RSV) in a biological sample, including the steps of a) amplifying a nucleic acid sequence encoding an RSV open reading frame (ORF) in a biological sample using a primer that comprises SEQ ID NO:1, a primer that comprises SEQ ID NO:2, and either a probe that comprises SEQ ID NO:3 or a probe that comprises SEQ ID NO:4 in a quantitative polymerase chain reaction assay, wherein the probe is labeled; and b) determining the presence or absence of an amplification product that binds the probe, or determining the viral load, thereby determining the RSV genotype(s) present or viral load of the RSV in the biological sample.

Also provided are methods for diagnosing an RSV infection in a subject. These methods may include the steps of a) amplifying a nucleic acid sequence encoding an RSV ORF in a biological sample from the subject using a set of primers that specifically amplifies an RSV subtype A ORF and/or an RSV subtype B ORF and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled; and b) determining the viral load and the RSV subtype(s) present in the biological sample, thereby diagnosing a subject with an RSV infection.

Methods for determining the efficacy of a therapy for RSV infection in a subject also are provided. These methods may include the steps of amplifying a nucleic acid sequence encoding an RSV ORF in a first biological sample from the subject using a set of primers that specifically amplifies an RSV subtype A ORF and/or an RSV B ORF and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled; b) determining the viral load and the RSV subtype(s) present in the first biological sample; c)

amplifying a nucleic acid sequence encoding an RSV ORF in a second biological sample from the subject using a set of primers that specifically amplifies an RSV subtype A ORF and/or an RSV subtype B ORF and at least two nucleic acid probes in a quantitative polymerase chain reaction assay, wherein the subject has undergone at least one treatment with a first therapy for RSV infection, wherein at least one probe specifically binds to an RSV subtype A nucleic acid sequence and at least one probe specifically binds to an RSV subtype B nucleic acid sequence, and wherein the at least two nucleic acid probes are differentially labeled; d) determining the viral load and the RSV subtype(s) present in the second biological sample; comparing the viral load and/or RSV subtypes of the first biological sample with the viral load and/or RSV subtypes of the second biological sample, wherein a decrease in viral load in the second biological sample or a change in RSV subtype(s) as compared to the viral load and/or subtypes in the first biological sample indicates that the treatment is effective and wherein an increase or no change in viral load and/or RSV subtype(s) or no change in the subtype(s) as compared to the viral load and/or RSV subtype (s) in the first biological sample indicates that the treatment is ineffective.

Nucleic acid probes for the detection of the genotype of an RSV are provided. In some embodiments, the probes comprise SEQ ID NO:3 or SEQ ID NO:4. In other embodiments, the probes comprise SEQ ID NO:36 (GCAAGCT-TAACAACTGAAATTCAAATCAAC) or SEQ ID NO:37 (TCAAGCTTGACATCAGAAATACAAGTCAAT). Methods are provided for using one or more of these probes for the detection of the genotype of an RSV in a biological sample. In some embodiments, a control probe is used. The control probe may comprise, for example, SEQ ID NO:5.

Kits are provided for the detection of viral load and the genotype of an RSV in a biological sample. The kits may include a nucleic acid primer comprising SEQ ID NO:1, a nucleic acid primer comprising SEQ ID NO:2, a probe comprising SEQ ID NO:3, and a probe comprising SEQ ID NO:4. In certain embodiments, the kits further comprise a nucleic acid primer comprising SEQ ID NO:34, a nucleic acid primer comprising SEQ ID NO:35, a nucleic acid probe comprising SEQ ID NO:36 and a nucleic acid probe comprising SEQ ID NO:37.

Also provided are methods for amplifying and sequencing the open reading frame (ORF) of an RSV F protein and methods for amplifying and sequencing the ORF of an RSV F protein. Certain of these methods may include the step of amplifying a nucleic acid sequence encoding an RSV F open reading frame in a biological sample using a set of primers comprising SEQ ID NO:6 and SEQ ID NO:7 in a polymerase chain reaction assay. In some embodiments, the methods further may include sequencing the amplification product using one or more primers selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19. Certain other methods may include the step of amplifying a nucleic acid sequence encoding an RSV F open reading frame in a biological sample using a set of primers comprising SEQ ID NO:8 and SEQ ID NO:9. In some embodiments, the methods may further include sequencing the amplification product in a polymerase chain reaction assay using one or more sequencing primers selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 and SEQ ID NO:29.

Further provided are kits for the amplification and sequencing the ORF of an RSV F protein and kits for the amplification and sequencing the ORF of an RSV F protein. The kits include a set of primers comprising SEQ ID NO:6 and SEQ ID NO:7 and/or a set of primers comprising SEQ ID NO:8 and SEQ ID NO:9. In some embodiments, the kits may include one or more primers selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 and SEQ ID NO:29

DESCRIPTION OF THE DRAWINGS

The figures provided herein are intended to illustrate certain embodiments and/or features of the compositions and methods, and to supplement any description(s) of the compositions and methods. The figures do not limit the scope of the compositions and methods, unless the written description expressly indicates that such is the case.

FIGS. 1A and 1B show the results of multiplex qRT-PCR assays to simultaneously determine viral load and subtype specificity of RSV. FIG. 1A is a graphical representation of the data shown in the table in FIG. 1B, with RSV subtype A data shown in the top panels and RSV subtype B data shown in the bottom panels.

FIG. 2 is a table showing the results of a comparative study of the qRT-PCR assay with GenMark Diagnostics RVP qualitative assay. The data shown represent the results of qRT-PCR reactions being performed in triplex.

FIG. 3 presents tables showing a proficiency panel for the multiplex qRT-PCR assay. The data are the result of 10-fold serial dilutions, triplicate samples of known viral load, reported in copies/mL. Known VL refers to the viral load as detected using a singleplex assay, and MGB 3plex refers to the multiplex qRT-PCR assay in which RSV subtype A, RSV subtype B, and control may be detected in the same assay. The data demonstrates that there is no loss in sensitivity in the multiplexed reaction.

FIG. 5 shows the input and output screens for the online calculator used to determine copy number for the RSV virus.

FIG. 7A is a schematic diagram showing the relative locations of the sequencing primers used to sequence the RSV F ORF using Sanger sequencing. FIG. 7B is a neighbor joining tree of the RSV A and RSV B samples derived from Illumina MiSeq analysis.

DESCRIPTION

Figure 4:
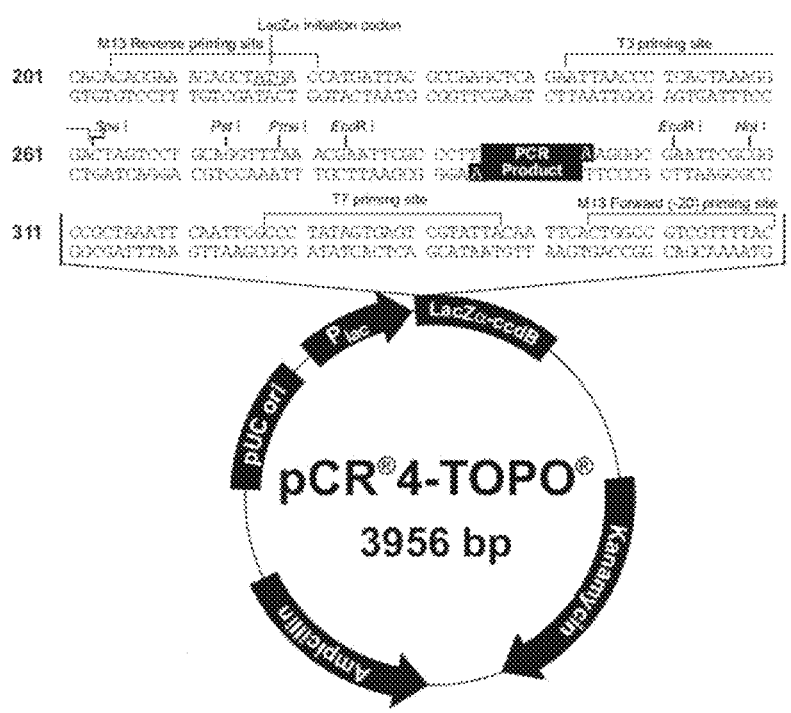
FIG. 4 is a schematic diagram of the cloning vector pCR'4-TOPO and the cloning site for the amplification product produced using universal primers that amplify the N region of RSV A2 and RSV B1.

Quantitative multiplex reverse transcriptase polymerase chain reaction (qRT-PCR) assay methods and compositions for use in these methods are provided. The present methods provide a sensitive and specific assay for the determination of viral load, genotyping of RSV, or both in a biological sample.

In certain embodiments, the methods use universal RSV amplification primers to amplify the desired sequence from both RSV subtypes A and B in the presence of differentially labeled RSV subtype A specific probes and RSV subtype B specific probes that are used to distinguish between each RSV strain. These qRT-PCR methods may be multiplex assays employing universal RSV amplification primers and differentially labeled RSV subtype A and RSV subtype B specific probes. These methods allow for the quantification of RSV viral load and the determination of the RSV subtype (A or B).

For example, provided herein are methods for simultaneously determining the viral load and genotype of a respiratory syncytial virus (RSV) in a biological sample. The methods include the steps of a) amplifying a nucleic acid sequence encoding an RSV open reading frame (ORF) in a biological sample using a set of primers that specifically amplifies an RSV subtype A ORF and/or an RSV subtype B ORF and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled; and b) determining the viral load and the RSV subtype(s) present in the biological sample. Alternatively, methods are provided for determining the genotype or viral load of a respiratory syncytial virus (RSV) in a biological sample, including the steps of a) amplifying a nucleic acid sequence encoding an RSV open reading frame (ORF) in a biological sample using a primer that comprises SEQ ID NO:1, a primer that comprises SEQ ID NO:2, a probe that comprises SEQ ID NO:3, and a probe that comprises SEQ ID NO:4 in a quantitative polymerase chain reaction assay, wherein the probes are differentially labeled; and b) determining the presence or absence of an amplification product that binds one of the probes, or determining the viral load, thereby determining the RSV genotype(s) present or viral load of the RSV in the biological sample. These methods also may be used for diagnosing a subject with RSV infection or for determining the efficacy of a treatment or vaccine for RSV.

As used herein, "a set of universal primers" is a set of nucleic acid primers that can specifically amplify an RSV subtype A (RSV A) nucleic acid and/or RSV subtype B (RSV B) nucleic acid, if an RSV A and/or an RSV B nucleic acid molecule is present in the biological sample. In the methods provided herein, the set of universal primers can include a pair of nucleic acid primers that specifically amplify a region of the RSV nucleocapsid (N) protein in RSV A and/or RSV B. Optionally, the set of universal primers that specifically amplify a region of the RSV nucleocapsid (N) protein in RSV A and/or RSV B includes a nucleic acid sequence comprising SEQ ID NO:1 and a nucleic acid sequence comprising SEQ ID NO:2. Other primers that can be used include, but are not limited to a nucleic acid comprising SEQ ID NO:34 (RGAAATGAAAT-TYGAAGTRTTAAC) and a nucleic acid comprising SEQ ID NO:35 (GARTCATGCCTRTATTCTGGAGC).

As used herein, the term "primer" refers to an oligonucleotide that can initiate 5' to 3' synthesis of a primer extension product that is complementary to a nucleic acid strand. In the methods provided herein, the set of primers contains a forward primer and a reverse primer.

As used herein, the term "probe" refers to an oligonucleotide that forms a hybrid structure with a target sequence, for example, an RSV A or an RSV B sequence, contained in a biological sample, due to complementarity of at least one sequence in the probe with the target sequence. The nucleotides of any particular probe can be ribonucleotides, deoxyribonucleotides, and/or synthetic nucleotide analogs. Examples of nucleic acid probes that can be used in the methods provided herein include, but are not limited to, a nucleic acid probe comprising SEQ ID NO:3 or SEQ ID NO:36 (GCAAGCTTAACAACTGAAATTCAAATCA) that specifically binds to an RSV subtype A nucleic acid sequence and a nucleic acid probe comprising SEQ ID NO:4 or SEQ ID NO:37 (TCAAGCTTGACATCAGAAATA-CAAGTCAAT) that specifically binds to an RSV subtype B nucleic acid sequence.

As used herein, the term "complementary" or "complementarity" refers to base pairing between nucleotides or nucleic acids. Examples include base pairing between an oligonucleotide primer and a primer binding site on a single-stranded nucleic acid to be sequenced or amplified and base pairing between a probe and a target nucleic acid sequence. Complementary nucleotides are, generally, adenine (A) and thymine (T) (or A and uracil (U)), and guanine (G) and cytosine (C). It is understood that the specific nucleotide sequence lengths provided herein are exemplary and not limiting. Further, sequences covering the same positions or locations within a RSV sequence, for example, positions of the nucleotide sequence encoding the RSV N protein or the RSV F protein, but having a fewer or greater number of bases as compared to the primer or probe sequences provided herein, are also contemplated herein provided that the sequences hybridize to the same locations on the target RSV A and/or RSV B sequence as the disclosed sequences. Those of skill in the art will appreciate that nucleic acids do not require 100% complementarity in order to hybridize. Therefore, probe and primer sequences that have about 80%, about 85%, about 90%, or about 95% identity with the probe and primer sequences provided herein can also be used in the methods described herein.

In the methods set forth herein, numerous methods are available in the art for determining viral load. For example, and not to be limiting, qRT-PCR can be used to quantify the amount of RSV virus, i.e., viral load, viral burden, or viral titer, in a biological sample. qRT-PCR methods for determining viral load are known in the art. (See for example, Payungporn et al. "Single step multiplex real-time RT-PCR for H5N 1 influenza A virus detection." *J Virol Methods*. Sep. 22, 2005; Landolt et la. "Use of real-time reverse transcriptase polymerase chain reaction assay and cell culture methods for detection of swine influenza A viruses" *Am J Vet Res*. 2005 January; 66(1):119-24). Those of skill in the art understand that RT-PCR assesses the kinetics of amplification, which is based on the starting template copy number. The metric is Ct, which stands for cycle threshold. Ct is a relative measure of the concentration of target in the PCR reaction that represents the computed amplification cycle at which point the detection of released fluorophore statistically exceeds the background fluorophore signal (the inflection point of fluorophore signal generation). In other words, Ct is the number of cycles required for the fluorescent signal to cross the threshold, i.e., exceed background level. One of skill in the art would know how to establish Ct cut-off values for positivity as well as generate standard curves for viral load quantitation. Other methods include, but are not limited to digital PCR and transcription loop-mediated isothermal amplification (LAMP). These and other methods developed in the future for amplification and detection of nucleic acids can be used in the methods provided herein.

In the methods set forth herein, the RSV sequences in the biological sample can be reverse transcribed prior to amplification. Alternatively, the RSV sequences in the biological sample can be reverse transcribed and amplified in a single step.

By using differentially labeled probes for RSV A and RSV B, the production of amplification products during each cycle of the PCR reaction can be monitored, thus allowing discrimination between multiple viral genotypes and quantification of each genotype. In the methods described herein, the probes and/or primers can be labeled. Labels include atoms and molecules that are attached to a nucleic acid in order to produce a signal that is detectable and quantifiable by fluorescence, chemiluminescence, radioactivity, colorimetry, mass spectrometry, X-ray diffraction, absorption, magnetism, enzymatic activity, and the like. Examples of labels include fluorophores, chromophores, radioactive atoms, enzymes, and ligands having specific binding partners.

For example, and not to be limiting, probes can be labeled with donor and corresponding acceptor fluorescent moieties. Examples of fluorescent donor moieties include, but are not limited to FAM™ (fluorescein, blue), VIC® (asymmetric xanthene dye, green), and NED™ (yellow, Applied Biosystems) fluorescent dyes. Examples of fluorescent acceptor moieties include, but are not limited to, BHQ® (black hole quencher, Integrated DNA Technologies) and ZEN™ (dark quencher, Integrated DNA Technologies). These and other fluorescent moieties for use in RT-PCR are known to those of skill in the art and are available from numerous commercial sources.

As set forth above, the methods provided herein can optionally include amplification and detection of a recovery control. For example, the methods provided herein can include a set of primers that specifically amplifies a bacteriophage MS2 region and a nucleic acid probe that specifically binds to a bacteriophage M2 nucleic acid. Examples of primers that can be used to amplify an MS2 region include a nucleic acid sequence comprising SEQ ID NO:30 and a nucleic acid sequence comprising SEQ ID NO:31. An example of a probe that can be used to detect an MS2 nucleic acid is set forth herein as SEQ ID NO:5.

A recovery control can include a nucleic acid molecule from a different source other than an RSV molecule. For example, a recovery control can include a nucleic acid from a different virus or bacteriophage, such as MS2. One of skill in the art would know how to design primers that specifically amplify a control amplification product and probes that specifically detect the recovery control amplification product. The methods provided herein also may include separate samples that include one or more positive control samples that include RSV A and/or RSV B sequences.

Any of the methods of determining viral load and/or RSV subtype(s) described herein can further comprise amplifying the RSV F open reading frame in a biological sample and b) sequencing the amplification product. Methods, primers for amplification, and primers for sequencing of RSV A and RSV B F open reading frames are set forth below. Thus, sequencing of the RSV F protein can be used to confirm the subtypes identified in the methods provided herein.

As used herein, a biological sample is a sample derived from a subject such as a mammal or human and includes, but is not limited to, any biological fluid, including a bodily fluid. Examples of bodily fluids include, but are not limited to, whole blood, plasma, serum, urine, saliva, ocular fluid, ascites, sputum, throat swabs, throat washings, nasal swabs, lower respiratory tract specimens, a stool sample, spinal fluid, tissue infiltrate, pleural effusions, lung lavage fluid, and the like. The biological fluid includes a cell culture medium or supernatant of cultured cells from the subject.

As used throughout, the term "subject" refers to an individual. Preferably, the subject is a mammal such as a primate, and, more preferably, a human of any age, including a newborn or a child. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses are contemplated herein.

Also provided are methods for diagnosing an RSV infection in a subject. The methods include the steps of a) amplifying a nucleic acid sequence encoding an RSV ORF in a biological sample using a set of primers that specifically amplifies an RSV subtype A ORF and/or an RSV subtype B ORF and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled; and b) determining the viral load and the RSV subtype(s) present in the biological sample, thereby diagnosing a subject with an RSV infection.

The methods of diagnosing a subject with an RSV infection can further comprise treating the subject for an RSV infection. Antiviral drugs such as ribavirin, motavizumab, palivizumab (Synagis®), GS1, GS-5806 (See Jordan et al. "Antiviral Efficacy of Respiratory Syncytial Virus (RSV) Fusion Inhibitor in a Bovine Model of RSV Infection," 59 (8): 4889-4900 (2015) which is hereby incorporated in its entirety by this reference, particularly as it relates to the structures and activities of GS1 and GS-5806.), VP14637 and JNJ-2408068 (See Douglas et al. "Small Molecules VP-1637 and JNJ-2408068 Inhibit Respiratory Syncytial Virus Fusion by Similar Mechanisms," 49(6):2460-2466 (2005), which is hereby incorporated in its entirety by this reference, particularly as it relates to for the structures and activities of VP14637 and JNJ-2408068) can be used to treat RSV infections. As used herein, the terms treatment, treat, or treating refers to a method of reducing the effects of a disease or condition or symptom of the disease or condition. Thus, in the disclosed methods, treatment can refer to an about 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is an about 10% reduction in one or more symptoms of the disease in a subject as compared to a control. A control subject can be a subject that has not been treated for an RSV infection. Thus, the reduction can be an about 10%, 20%, 30%, 40%, 50%, 60%, 70%, 80%, 90%, 100%, or any percent reduction in between about 10% and 100% as compared to native or control levels. It is understood that treatment does not necessarily refer to a cure or complete ablation of the disease, condition, or symptoms of the disease or condition.

Further provided are methods for determining the efficacy of a therapy for RSV infection in a subject. The methods may include a) amplifying a nucleic acid sequence encoding an RSV ORF in a first biological sample from the subject using a set of primers that specifically amplifies an RSV subtype A ORF and/or an RSV subtype B ORF and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled; b) determining the viral load and the RSV subtype(s) present in the first biological sample; c) amplifying a nucleic acid sequence encoding an RSV ORF in a second biological sample from the subject using a set of primers that specifically amplifies an RSV subtype A ORF and/or an RSV subtype B ORF and at least two nucleic acid probes in a quantitative polymerase chain reaction assay, wherein the subject has undergone at least one treatment with a first therapy for RSV infection, wherein at least one probe specifically binds to an RSV subtype A nucleic acid sequence and at least one probe specifically binds to an RSV subtype B nucleic acid sequence, and wherein the at least two nucleic acid probes are differentially labeled; d) determining the viral load and the RSV subtype(s) present in the second biological sample; e) comparing the viral load and/or RSV subtypes of the first biological sample with the viral load and/or RSV subtypes of the second biological sample, wherein a decrease in viral load and/or a change in the subtype(s) in the second biological sample as compared to the viral load and/or the subtype(s) in the first biological sample indicates the treatment is effective and wherein an increase or no change in viral load and/or no change in the subtype(s) as compared to the viral load and/or subtype (s) in the first biological sample indicates the treatment is ineffective.

The methods of determining the efficacy of a therapy can also be used during treatment. For example, a first biological sample can be obtained from the subject after the first treatment for an RSV infection and a second biological sample can be obtained from the subject after the second treatment for an RSV infection in order to determine the difference in viral load and/or the amount of an RSV subtype(s), if any, between the first and second biological sample. Similarly, a first biological sample can be obtained from the subject after the second treatment for an RSV infection and a second biological sample can be obtained from the subject after the third treatment for an RSV infection in order to determine the difference in viral load and/or the amount of an RSV subtype(s), if any, between the second and third biological sample.

The decrease in viral load does not have to be complete as this decrease can be about a 10%, 20%, 30%, 40%, 50%, 60%, 70%, 80%, 90%, or 100% reduction in viral load. The decrease in viral load can also be a $\log_{10}$ decrease, for example, a 3-log decrease, a 4-log decrease, a 5-log decrease, or greater. If there is an increase or no change in viral load the type, dosage and/or frequency of the therapy can be modified for the subject.

Further provided are methods for determining the efficacy of an RSV vaccine in a subject. The methods include a) administering an RSV vaccine to a subject; b) contacting the subject with an RSV virus; b) amplifying a nucleic acid sequence encoding an RSV ORF in a biological sample from the vaccinated subject using a set of primers that specifically amplifies an RSV subtype A ORF and/or an RSV subtype B ORF and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled; c) determining the viral load and the RSV subtype(s) present in the biological sample; and d) comparing the viral load and/or RSV subtypes of the biological sample with the viral load and/or RSV subtypes of a control sample, wherein the control sample is from a subject that was contacted with the RSV virus and was not vaccinated with the RSV vaccine, wherein a decrease in viral load and/or a change in the subtype(s) in the biological sample as compared to the viral load and/or the subtype(s) in the control sample indicates the vaccine is protective and wherein an increase or no change in viral load and/or no change in the subtype(s) as compared to the viral load and/or subtype (s) in the first biological sample indicates the vaccine is not protective.

Protection does not have to be complete as the decrease in viral load can be about a 10%, 20%, 30%, 40%, 50%, 60%, 70%, 80%, 90%, or 100% reduction in viral load. The decrease in viral load can also be a $\log_{10}$ decrease, for example, a 3-log decrease, a 4-log decrease, a 5-log decrease, or greater.

The methods of determining the efficacy of a therapy for RSV infection or the efficacy of an RSV vaccine can further comprise the steps of determining the sequence of the RSV F open reading frame from the biological sample before treatment, determining the sequence of the RSV F open reading frame after treatment and comparing the sequences. If changes in the sequence occur after treatment, for example, mutations associated with resistance to a particular therapy, this would indicate that the subject could develop resistance to the therapy. These changes in the F protein sequence can be monitored in the subject as treatment progresses. The type, dosage, and/or frequency of the therapy can be modified for the subject based on changes in the F protein nucleic acid sequence.

Sequencing of RSV Isolates

Methods for sequencing RSV isolates are provided. More specifically, provided herein are methods for amplifying and sequencing the open reading frame (ORF) of the RSV F protein from RSV subtype A and/or RSV subtype B. Certain methods include the step of a) amplifying a nucleic acid sequence encoding an RSV F open reading frame in a biological sample using a set of primers comprising SEQ ID NO:6 and SEQ ID NO:7. In some embodiments of these methods, the methods further include the step of b) sequencing the amplification product using one or more primers selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19. Cycle sequencing is method in which successive rounds of PCR (denaturation, annealing and extension) in a thermal cycler result in linear amplification of extension products that are then loaded onto a gel or injected into a capillary for sequence analysis. As set forth in the Examples, the RSV F open reading frame is reverse transcribed prior to amplification. After amplification of the RSV F open reading frame, full-length sequencing may be performed with ten overlapping primers per subtype.

Also provided are methods for amplifying and sequencing the open reading frame (ORF) of the RSV F protein including the step of a) amplifying a nucleic acid sequence encoding an RSV F open reading frame in a biological sample using a set of primers comprising SEQ ID NO:8 and SEQ ID NO:9. In some embodiments of these methods, the methods further include the step of b) sequencing the amplification product using one or more primers selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 and SEQ ID NO:29. As set forth in the Examples, the RSV F open reading frame is reverse transcribed prior to amplification. After amplification of the RSV F open reading frame, full-length sequencing may be performed with ten overlapping primers per subtype.

In the sequencing methods provided herein, the amplification product can be sequenced using any method, including but not limited to, cycle sequencing, Maxam-Gilbert sequencing, Sanger sequencing, next generation sequencing, and the like. Therefore, in some embodiments, for example, a nucleic acid sequence encoding an RSV F open reading frame in a biological sample is amplified using a set of primers comprising SEQ ID NO:6 and SEQ ID NO:7 or a set of primers comprising SEQ ID NO:8 and SEQ ID NO:9, and the amplification product is sequenced by next generation sequencing analysis.

Probes and Kits

Nucleic acid probes for the detection of the genotype of an RSV are provided. In some embodiments, the probes comprise SEQ ID NO:3 or SEQ ID NO:4. In other embodiments, the probes comprise SEQ ID NO:36 or SEQ ID NO:37. Methods are provided for using one or more of these probes for the detection of the genotype of an RSV in a biological sample.

Also provided is a kit for the detection of viral load and the genotype of an RSV in a biological sample comprising a set of nucleic acid primers that specifically amplifies the N region of the RSV A subtype (RSV A) and the RSV B subtype (RSV B), a nucleic acid probe that specifically binds to an RSV A nucleic acid and a nucleic acid probe that specifically binds to an RSV B nucleic acid. For example, the kit can include a nucleic acid primer comprising SEQ ID NO:1 and a nucleic acid primer comprising SEQ ID. NO: 2 for amplification of the N region of RSV A and the RSV B subtypes as well as a probe comprising SEQ ID NO:3 that specifically binds to RSV A nucleic acid sequence and a probe comprising SEQ ID NO:4 that specifically binds to a RSV B nucleic acid sequence. In another embodiment, the kit can include a nucleic acid primer comprising SEQ ID NO:34 and a nucleic acid primer comprising SEQ ID NO:35 for amplification of the N region of RSV A and the RSV B subtypes as well as a probe comprising SEQ ID NO:36 that specifically binds to RSV A nucleic acid sequence and a probe comprising SEQ ID NO:37 that specifically binds to a RSV B nucleic acid sequence. In some embodiments, the kit further includes a primer comprising SEQ ID NO:30, a nucleic acid primer comprising SEQ ID NO:31, and a nucleic acid probe comprising SEQ ID NO:5. Optionally, one or more of the primers and/or probes can be labeled with different, detectable labels.

Also provided is a kit for the amplification and sequencing of an RSV F ORF. The kit includes an amplification primer comprising SEQ ID NO:6 and an amplification primer comprising SEQ ID NO:7. The kit may further include one or more primers selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19. Optionally, one or more of the primers can be labeled with the same or different detectable labels. Optionally, the kit further comprises reagents for isolating and/or sequencing the DNA in the sample.

Further provided is a kit for the amplification and sequencing of an RSV F ORF. The kit includes an amplification primer comprising SEQ ID NO:8 and an amplification primer comprising SEQ ID NO:9. The kit may further include one or more primers selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28 and SEQ ID NO:29. Optionally, one or more of the primers can be labeled with the same or different detectable labels. Optionally, the kit further comprises reagents for isolating and/or sequencing the DNA in the sample.

Disclosed are materials and compositions that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following non-limiting examples are intended to illustrate certain embodiments and/or features of the compositions and methods and to supplement any description(s) of the compositions and methods.

Example 1

Total Nucleic Acid Purification

The nucleic acids were purified from RSV from biological samples using the Biomerieux NucliSENS easyMAG® system. The materials for nucleic acid purification included the following:
  NucliSENS easyMag instrument
  easyMag Wash Buffers 1, 2, 3
  easyMag Lysis Buffer
  easyMag Magnetic Silica
  Respiratory samples (~200 µl)

The nucleic acid purification was performed as follows. Twenty-two samples were equilibrated to room temperature under a laminar flow hood. The NucliSENS easyMAG unit was turned on before logging into the software. A series was prepared as follows: the sample type was selected (other), the extraction protocol was selected (Generic 2.0.1), the sample volume was selected (200 µl), the elution volume of each sample was selected (50 µl), and the type of lysis was selected (on-board).

Samples to be processed were identified. The first icon to the right was clicked in order to choose whether incubation lysis must be performed by the instrument NucliSens easy- MAG or outside ('on board' or 'off board'). For the incubation with silica, 'on board' was selected. All samples were selected and 'Add selected samples to run' was selected. The barcode of the reagents was entered with the reader by first clicking on the barcode of the machine and then on the bottle. Then 200 µl of sample were placed in each well of a disposable (8-well plastic cartridge) in the laminar flow hood. Three disposables and their suction combs were installed on the instrument by first scanning the bar code of the position and then the bar code of the disposable. Ten µl of internal control MS2 was added per well of disposable. Delivery of lysis buffer was initiated.

The extraction protocol for off-board lysis was performed using the NucliSens easyMAG Total Nucleic Acid Extraction standard protocol. Dry swabs were re-suspended by adding 1,500 µL of the suspension buffer (easyMAG Lysis Buffer, UTM, saline solution, AVE buffer, or RNAlater). All samples were vortexed vigorously for 15 seconds at least three times. Some of the supernatant was used for nucleic acid extraction. The remaining supernatant was transferred to a 2 mL microcentrifuge tube for long term storage. The sample input volume for nucleic acid extraction was 500 µL with an elution output of 100 µL. During the lysis stage, 550 µl of RNAse-free ddH$_2$O was combined with 550 µl Magnetic Silica and mixed thoroughly. Then 125 µl of silica was added per well and mixed with a multichannel pipette. The extraction procedure was launched, and the extracted nucleic acids were collected in the half-hour after the end of the run. The extracted nucleic acids were transferred to sterile 1.5 ml tubes used directly or stored at −80° C.

Example 2

Determination of Consensus Sequence for the RSV N Open Reading Frame

Consensus sequences based on the top 100 hits for an RSV A2 and B1 N (open reading frame) ORF reference sequences were obtained. Both consensus sequences are set forth below.

```
RSV A2 N ORF consensus
                                              (SEQ ID NO: 32)
ATGGCTCTTAGCAAAGTCAAGTTGAAYGATACACTCAACAAAGATCAAC

TTCTGTCATCCAGCAAATACACCATCCAACGGAGCACAGGAGAYAGYAT

TGAYACTCCTAATTATGATGTGCAGAAACACATCAAYAAGYTATGTGGC

ATGTTATTAATCACAGAAGATGCTAATCATAAATTCACTGGGKTAATAG

GTATGTTATATGCTATGTCTAGATTAGGAAGAGAAGACACCATAAAAAT

ACTCARAGATGCDGGATATCATGTAAAAGCWAATGGAGTGGATGTAACA

ACACATCGTCAAGAYATTAATGGRAAAGAAATGAAATTTGAAGTGTTAA

CATTRGCAAGCTTAACAACTGAAATTCAAATCAACATTGAGATAGAATC

TAGRAAATCCTACAAAAAAATGCTAAAAGAAATGGGAGAGGTRGCTCCA

GAATACAGGCATGACTCWCCTGATTGTGGRATGATAATATTATGTATAG

CRGCATTAGTAATAACCAAATTAGCAGCAGGGGATAGATCTGGTCTTAC

AGCYGTRATTAGGAGAGCTAATAATGTYCTAAAAAATGAAATGAAACGT

TATAAAGGCTTACTACCHAAGGATATAGCHAACAGYTTCTATGAAGTGT

TTGAAAAATATCCTCACTTTATAGATGTTTTTGTTCATTTTGGTATAGC

ACAATCTTCTACCAGAGGTGGCAGTAGAGTTGAAGGGATTTTTGCAGGA

TTGTTTATGAATGCCTATGGTGCAGGGCAAGTGATGTTACGGTGGGRGT

CTTAGCAAAATCAGTTAAAAATATTATGYTAGGACACGCTAGTGTGCAA

GCAGAAATGGAACAAGTTGTGGARGTDTATGAATATGCCCAAAAATTGG

GTGGAGAAGCAGGATTCTACCATATATTGAAYAACCCAAAAGCATCATT

ATTATCTTTGACTCAATTYCCYCACTTCTCYAGTGTAGTATTRGGCAAT

GCTGCTGGCCTAGGCATAATGGGAGAATACAGAGGTACACCAAGGAATC

AAGATCTATATGATGCTGCDAARGCATATGCTGAACAACTCAAAGAAAA

TGGTGTGATTAACTACAGTGTATTAGACTTGACAGCAGAAGAACTAGAG

GCTATCAAACATCAGCTTAATCCAAAAGATAATGATGTAGAGCTTTGA

RSV B1 N ORF consensus
                                              (SEQ ID NO: 33)
ATGGCTCTTAGCAAAGTCAAGTTRAATGATACATTAAATAAGGATCAGC

TGCTGTCATCCAGCAAATACACTATTCAACGTAGTACAGGAGATAATAT

TGACACTCCCAATTATGATGTRCAAAAACACYTAAACAAACTATGTGGT

ATGCTATTAATCACTGAAGATGCAAATCATAAATTCACAGGATTAATAG

GTATGYTATATGCTATGTCCAGGTTAGGAAGGGAAGACACTATAAAGAT

ACTTAAAGATGCTGGATATCATGTTAAAGCTAATGGAGTAGATATAACA

ACATATCGTCAAGATATAAATGGAAAGGAAATGAAATTCGAAGTATTAA

CATTATCAAGCTTGACATCAGAAATACAAGTCAATATTGAGATAGAATC

TAGAAAGTCCTACAAAAAAATGCTAAAAGARATGGGAGAAGTGGCTCCA

GAATATAGGCATGAYTCTCCAGACTGTGGGATGATAATACTRTGTATAG

CWGCHCTTGTVATAACCAAATTAGCAGCAGGAGAYAGATCAGGTCTYAC

AGCAGTAATTAGGAGRGCRAACAATGTCTTAAAAAACGAAATAAAACGH

TACAAGGGCCTVATACCAAAGGAYATAGCYAACAGTTTTTATGAAGTGT

TTGAAAAACACCCTCATCTTATAGATGTTTTYGTGCACTTTGGCATTGC

ACAATCATCCACAAGAGGGGGTAGTAGAGTTGAAGGAATCTTTGCAGGA

TTRTTTATGAATGCCTATGGTTCAGGRCAAGTAATGCTAAGATGGGGAG

TTTTAGCCAAATCTGTAAAAAATATCATGCTAGGWCATGCTAGTGTCCA

RGCAGAAATGGAGCAAGTTGTDGAAGTCTATGAGTATGCACAGAAGTTG

GGRGGAGAAGCTGGWTTCTACCATATATTGAACAATCCAAAAGCATCAT

TGCTGTCATTAACTCAATTTCCYAACTTCTCAAGTGTGGTCCTAGGCAA

TGCAGCAGGYCTAGGCATAATGGGAGAGTATAGAGGTACACCAAGAAAC

CARGATCTYTATGATGCWGCCAAAGCATATGCAGAGCAACTCAAAGAAA

ATGGAGTAATAAACTACAGTGTATTAGACTTAACARCAGAAGAATTGGA

AGCCATAAAGMATCAACTCAACCCCAAAGAAGATGAYGTAGAGCTYTAA
```

Example 3

Determination of Genotype Using Quantitative Real-Time PCR (qRTPCR) Assay

Primers that specifically amplify the N region of both the RSV A2 and the RSV B1 subtypes were designed using the consensus sequences described. The sequences for these primers (RSV499 and RSV636) are set forth below in Table 1. Alternate primers for specifically amplifying the N region of both RSV A and RSV B subtypes are RSV322 and RSV458.

A probe that specifically binds to an RSV A nucleic acid sequence (RSVA576) and a probe that specifically binds to an RSV B (RSVB576) nucleic acid sequence also were designed. Alternate probes for specifically binding RSV A nucleic acid sequences or RSV B nucleic acid sequences are RSVA349 and RSVB349, respectively. The sequences for these probes are shown in Table 1.

For use as controls, a primer pair that amplifies an M2 sequence (MS2F and MS2R) and a probe that specifically binds to an M2 nucleic acid sequence were designed. The sequences for these primers and this probe are shown in Table 1.

closed and the tubes quickly spun to collect all liquids. The tubes were placed in the thermocycler, and the following reaction conditions were used:

| | | |
|---|---|---|
| RT reaction (cDNA synthesis) | 50° C. | 10 min |
| RT inactivation | 95° C. | 10 min |
| PCR 40 cycles | | |
| Denature | 95° C. | 15 sec |
| Anneal | 45° C. | 45 sec |

The RT-PCR amplicon resulting from amplification with primers RSV499 and RSV636 was about 137 bp. The qRT-PCR assay provided the desired sensitivity in the 7 $\log_{10}$ dynamic range; Lower limit of detection (LLOD) ~100

TABLE 1

Sequences for RSV and MS2 (recovery control) primers and probes

| | |
|---|---|
| RSV499 | GTV ATA ACC AAA TTA GCA GC (SEQ ID NO: 1) |
| RSV636 | CAC TTC ATA RAA RCT GTT DGC (SEQ ID NO: 2) |
| RSV322 | RGAAATGAAATTYGAAGTRTTAAC (SEQ ID NO: 34) |
| RSV458 | GARTCATGCCTRTATTCTGGAGC (SEQ ID NO: 35) |
| RSVA576 | VIC ®/TGA AAT GAA ACG TTA TAA AGG CTT AC/BHQ ® (SEQ ID NO: 3) |
| RSVB576 | FAM ™/CGA AAT AAA ACG HTA CAA GGG CCT VA/ZEN ™ (SEQ ID NO: 4) |
| RSVA349 | VIC ®/GCAAGCTTAACAACTGAAATTCAAATCAAC/BHQ ® (SEQ ID NO: 36) |
| RSVB349 | FAM ™/TCAAGCTTGACATCAGAAATACAAGTCAAT/ZEN ™ (SEQ ID NO: 37) |
| MS2F | TGT GGA GAG AC A GGG CAC TG (SEQ ID NO: 30) |
| MS2R | CAG TTG TTG GCC ATA CGG ATT (SEQ ID NO: 31) |
| MS2probe | NED ™/TAA GGC CCA AAT CTC AGC CAT GCA TC/BHQ ® (SEQ ID NO: 5) |

The materials that were used for the viral load quantification included RSV RNA samples, primer and probes (10 µM each), and ThermoFisher Ag-Path ID One-Step RT-PCR (Catalogue No. A M1005M).

The RSV load quantification was performed as follows. The RNA templates, primers, probes, and 2× reaction mix were thawed at room temperature and immediately placed on ice once thawed. Enzyme was kept at −20° C. until ready to use. The RT-PCR mastermix was prepared on ice using the sample volume below:

| | Volume | Final concentration |
|---|---|---|
| 2x reaction mix | 12.5 µl | |
| Forward primer-RSV | 0.5 µl | 200 nM |
| Reverse primer-RSV | 0.5 µl | 200 nM |
| Forward primer-MS2 | 0.25 µl | 100 nM |
| Reverse primer-MS2 | 0.25 µl | 100 nM |
| Probe-RSVA/VIC ® | 0.25 µl | 100 nM |
| Probe-RSVB/FAM ™ | 0.5 µl | 200 nM |
| Probe-MS2/NED ™ | 0.25 µl | 100 nM |
| Water | 7.5 µl | |
| 25x enzyme mix | 1.5 µl | |
| Total | 25 µl (when the RNA template 1 µl is added) | |

The required mastermix was aliquoted into each PCR tube. One µl of RNA template was added into its designated tube, and water was used as a negative control. The lids were copies. The assay also provided desired subtype specificity. As shown in FIG. 1, RSV A and RSV B are detectable and quantifiable in a multiplexed reaction.

To determine whether the qRT-PCR assay was able to provide genotyping results comparable to commercially available qualitative assays, testing of RSV samples was performed with either the present qRT-PCR assay or with the GenMark Diagnostics RVP qualitative assay. The results of the comparative study with GenMark Diagnostics RVP qualitative assay are shown in FIG. 2. The data shown in the tables is the result of reactions that were performed in triplicate. The left table shows the quantitative results using the qRT-PCR assay with two known RSV A samples (PC1_A and PC2_A), two known RSV B samples (PC1_B and PC2_B), and two controls that did not include a template. The numbers shown are the Ct values, which indicate the copy number present in the sample. UND indicates that the particular RSV type was not detected in the reaction. The data in the right two tables shows qualitative results of the qRT-PCR assay and the GenMark RVP assay. Notably, one RSV sample was able to be genotyped by the present qRT-PCR assay, but was not detected or typed by the GenMark RVP assay.

These results show that a multiplex RSV A and RSV B specific viral load and typing assay that includes a recovery control was successfully developed. The accuracy of RSV typing was confirmed based on concordance with an FDA-cleared test as well as F gene sequencing.

A proficiency panel was conducted to assess the sensitivity of the multiplex qRT-PCR assay, and the results are shown in FIG. 3. The figure presents tables showing data that are the result of triplicate samples of known viral load, reported in copies/mL. Known VL refers to the known viral load as detected using a singleplex assay, and MGB 3plex refers to the assay in which the subtype A probes, subtype B probes, and control probes are included in the same reaction. The data demonstrates that there is no loss in sensitivity in the multiplexed reaction.

Example 4

Quantitation of Viral Load

Commercially available RSV kits thus far have only been qualitative. As set forth in the following example, an RSV triplex qRT-PCR assay was developed that quantifies RSV viral load (copies/ml), subtypes for RSV A/B strains and is formatted to detect an internal control. The accuracy of the quantitation of the qRT-PCR assay was analyzed using an in vitro transcript (IVT) control. The RT-PCR amplicon resulting from primers RSV499 and RSV636 described above was cloned into a plasmid. The amplicon was gel purified and cloned according to the manufacturer's protocol (ThermoFisher, Catalogue No. K4575-02) into pCR®4-TOPO (FIG. 4) to create the pCR4-TOPO-RSVA2.N plasmid and the pCR4-TOPO-RSVB1.N plasmid. These vectors were used in an in vitro transcription assay, along with the ThermoFisher MEGAscript T7 Transcription kit (Catalogue No. AM1334), the ThermoFisher MEGAclear kit (Catalogue No. AM1908), and New England BioLabs (Ipswich, Mass.) SpeI restriction enzyme.

The DNA concentration of each plasmid was measured, and 10 µg of each plasmid was linearized using the following digestion conditions:

| | |
|---|---|
| 10 µg DNA | x µl |
| SpeI | 5 µl |
| Cutsmart buffer | 10 µl |
| Water | y µl |
| Total | 100 µl |

Linearization was verified on a 1% agarose gel. The gel purification protocol using QIAquick spin columns (Qiagen) was followed. At the elution step, the elution was performed with 23 µl RNAse free ddH$_2$O from the MEGAscript T7 transcription kit (optional: prewarmed to 55° C.). The MEGAscript T7 kit reagents (10× reaction buffer, ribonucleotides) were thawed, and T7 enzyme was kept at −20° C. The nucleotide and reaction buffer mastermix was prepared per sample volume below:

| | |
|---|---|
| ATP solution | 2 µl |
| CTP solution | 2 µl |
| GTP solution | 2 µl |
| UTP solution | 2 µl |
| 10× reaction buffer | 2 µl |

Then 10 µl of the mixture was distributed into tubes, and 8 µl of linearized DNA template and 2 µl of enzyme were added. The mix was pipetted and subjected to centrifugation if necessary. The reaction was incubated at 37° C. for 2 hours. One µl of TURBO DNAse mix was added, and the reaction was incubated for 15 minutes at 37° C. Meanwhile, a portion of the elution solution was heated to 95° C. Then 80 µl of elution solution (room temp) was added to each tube and mixed thoroughly.

Then 100 µl of sample was transferred to 350 µl of Binding Solution concentrate and mixed thoroughly. Ethanol (250 µl of a 100% solution) from a new bottle was added to each sample and mixed gently. Then 700 µl of the sample was added to a column (provided in kit) and spun at 13,000 RPM. The flow-through was discarded. The column was washed twice with 500 µl Wash Solution and spun for 4 minutes after the last wash to remove all traces of Wash Solution. Then 50 µl of Elution Solution (room temp) and 50 µl Elution Solution (95° C. heated) were added and incubated in the column for 1 minute. Elution was performed by spinning at 13,000 RPM into a new collection tube. Eluted RNA was stored at −80° C. Quality of the RNA was assessed (Agilent RNA 6000 Nano kit, Catalogue No. 5067-1511), and the yield was determined (ThermoFisher NanoDrop 2000c)(Palo Alto, Calif.). The RNA was approximately 220 nucleotides (nt) in length.

Copy Number Calculation

The number of RNA copies was determined using the following formula on the online calculator set forth below: copies=(ng*6.022×10$^{23}$/mole)/(length*1×10$^9$ ng/g*325 g/mole) The online calculator can be found at: www.endmemo.com/bio/dnacopynum.php.

The amount of purified RNA was measured on a ThermoFisher NanoDrop 2000c and determined to be 499 ng/µl for the RSV A2 in vitro transcript (IVT) and 584 ng/µl for the RSV B1 IVT.

Figure 5:
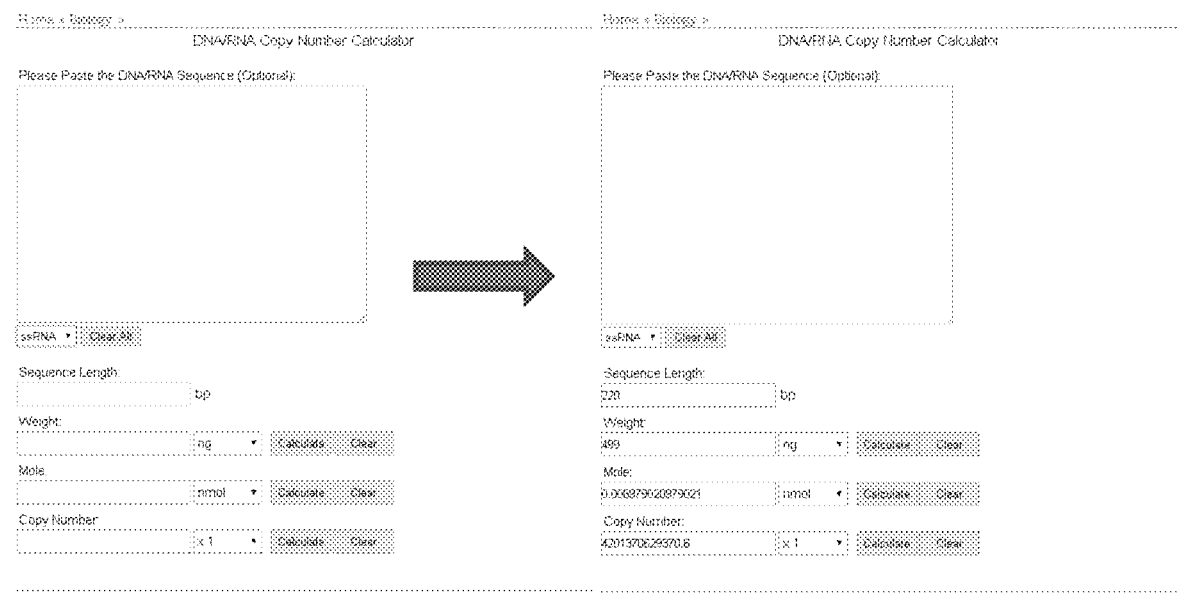

The following information was entered into the online calculator using the input screen shown in FIG. 5:

Choose option 'ssRNA'

Sequence length=200 nt

Weight=499 ng

Click 'calculate'

A dilution series was prepared as shown below:

(4.2×10$^{12}$ copies/µl)(x)=(5×10$^{10}$ copies/µl)(100 µl)

x=(5×10$^{10}$ copies/µl)/(4.2×10$^{12}$ copies/µl)

x=1.2 µl RSV A2 IVT+98.8 µl RNAse-free ddH$_2$O Then, serial 10-fold dilutions were made (for 1×10$^2$, make 1:5 of 5×10$^2$). The calculations and serial dilutions were repeated for RSV B1 IVT.

Example 5

Sequencing of RSV F ORF

The RSV A and B sequences were amplified using reverse transcription PCR (RT-PCR). The RSV A2 reference sequence can be found under GenBank Accession No. JX198138. The RSV B1 reference sequence can be found under GenBank Accession No. AF013254. Primers for reverse transcription and amplification of RSV A or RSV B were designed and are shown in Table 2.

TABLE 2

RSV F ORF reverse transcription primers:

| | |
|---|---|
| 5_RSV_A2 PCR primer | GGG CTC GAG ACC GGT TCT GGG GCA AAT AAC AAT GG (SEQ ID NO: 6) |
| 3_RSV_A2 RT and/or PCR primer | GGG TCT AGA ACG CGT TAG GTG CTA TTT TTA TTT AGT TAC (SEQ ID NO: 7) |
| 5_RSV_B1 PCR primer | GGG CTC GAG ACC GGT CCT GGG GCA AAT AAC CAT GG (SEQ ID NO: 8) |
| 3_RSV_B1 RT and/or PCR primer | GGG TCT AGA ACG CGT TCA GGT GGT TTT TTG TCT ATT TGC (SEQ ID NO: 9) |

The RNA samples were used in an RT-PCR assay using a 5' and 3' primer set (either A2 or B1) (10 µM each) and the ThermoFisher SuperScript III Kit with Platinum Taq (Catalogue No. 12574-026) (Waltham, Mass.).

The protocol for the RT-PCR of the RSV isolates included the following steps. RNA templates, primers, and 2× reaction mix were thawed at room temperature and immediately placed on ice once thawed. Enzyme was kept at −20° C. until ready to use. The RT-PCR mastermix was prepared on ice using per sample volume below:

| | |
|---|---|
| 2x reaction mix | 25 µl |
| Forward primer | 1 µl |
| Reverse primer | 1 µl |
| Water | 17 µl |
| SSIII/Taq | 1 µl |
| RNA template | 5 µl |
| Total | 50 µl |

The required mastermix was aliquoted into each PCR tube. The amount of RNA template was added into its designated tube, and water was used as a negative control. The lids were closed and the tubes were spun quickly to collect all liquids. The tubes were then placed in the thermocycler, and the reactions were run as follows:

| | | |
|---|---|---|
| RT reaction | 55° C. | 30 min |
| RT inactivation PCR 40 cycles | 94° C. | 2 min |
| Denature | 94° C. | 30 sec |
| Anneal | 55° C. | 30 sec |
| Extend | 68° C. | 3 min |
| Final extension | 68° C. | 5 min |
| Storage | 4° C. | indefinite |

The resulting RT-PCR amplicons were approximately 2800 bp. They were run on a 1% agarose gel, excised, and gel purified using the QIAquick gel extraction kit (Qiagen, Valencia, Calif., Catalogue No. 28704).

The purification included the following steps. Three volumes of Buffer QG were added to 1 volume of gel (100 mg=100 µl). The gel was incubated in the buffer at 50° C. for 10 minutes. After the gel had dissolved, the color of the mixture was checked to confirm it was yellow (similar to Buffer QG without dissolved agarose). One gel volume of isopropanol was added to each sample and mixed. DNA was bound into a QIAquick spin column and centrifuged at 13000 rpm for 1 minute. Flow-through was discarded. Columns were washed by adding 0.75 mL of Buffer PE and centrifuged for 1 minute. Flow-through was discarded, and the empty column was centrifuged for an additional minute. The QIAquick spin column was placed into a clean Eppendorf tube, the DNA was eluted in 40 µl Buffer EB, and the concentration of DNA was measured.

Sequencing primers were designed against A2 and B1 reference strains. Ten primers each were tested for the sequencing of the F open reading frame of RSV subtypes A and B. Forty-five RSV samples and 2 reference RSV strains were analyzed using the designed primers. The general position of the tested primers is shown in FIG. 5A and a neighbor joining tree of RSV A and RSV B samples tested in RSV sequencing assay is shown in FIG. 5B.

Tables 3 and 4 show the primers that were used for Sanger sequencing.

TABLE 3

RSV A2 F ORF sequencing primers:

| | |
|---|---|
| 440F.RSV.ENVS.A2 | CTC TGG GGC AAA TAA CAA TGG AGT TG (SEQ ID NO: 10) |
| 74F.RSV.ENVS.A2 | GTC AAA ACA TCA CTG AAG AAT TTT ATC (SEQ ID NO: 11) |
| 407R.RSV.ENVS.A2 | CTT CTT TTC CTT TTC TTG CTT AAT G (SEQ ID NO: 12) |
| 449R.RSV.ENVS.A2 | CTG GCG ATT GCA GAT CCA ACA CCT A (SEQ ID NO: 13) |
| 508F.RSV.ENVS.A2 | GCT CTA CTA TCC ACA AAC AAG GCT GTA GTC (SEQ ID NO: 14) |
| 792F.RSV.ENVS.A2 | GCC TAT AAC AAA TGA TCA GAA AAA G (SEQ ID NO: 15) |
| 867R.RSV.ENVS.A2 | CAT GAT AGA GTA ACT TTG CTG TCT AAC T (SEQ ID NO: 16) |

TABLE 3-continued

RSV A2 F ORF sequencing primers:

| | |
|---|---|
| 1043R.RSV.ENVS.A2 | GAT CCT GCA TTG TCA CAG TAC CAT CC (SEQ ID NO: 17) |
| 1480R.RSV.ENVS.A2 | GAG ATA TTG ATG CAT CAA ATT CAT C (SEQ ID NO: 18) |
| 1397F.RSV.ENVS.A2 | GTC TCT ATG TAA AAG GTG AAC CAA TA (SEQ ID NO: 19) |

TABLE 4

RSV B1 F ORF sequencing primers:

| | |
|---|---|
| 33R.RSV.ENVS.B1 | GAT TGC ACT TGA TCT ATG GAT CAG C (SEQ ID NO: 20) |
| 74F.RSV.ENVS.B1 | GTC AGA ACA TAA CTG AGG AGT TTT ACC (SEQ ID NO: 21) |
| 484R.RSV.ENVS.B1 | CTT CAA GGT GTA GAA CTT TGG ATA CAG (SEQ ID NO: 22) |
| 664F.RSV.ENVS.B1 | GAA TTC CAG CAG AAG AAC AGC AGA TTG (SEQ ID NO: 23) |
| 835F.RSV.ENVS.B1 | CAG ATA GTA AGG CAA CAA AG (SEQ ID NO: 24) |
| 901F.RSV.ENVS.B1 | GTA CAG CTA CCT ATC TAT GG (SEQ ID NO: 25) |
| 1104R.RSV.ENVS.B1 | GTC ACA AAA TAC TCG ATT GGA C (SEQ ID NO: 26) |
| 1174R.RSV.ENVS.B1 | CAT ACT TGG AAT TGA ATA TGT CAG (SEQ ID NO: 27) |
| 1121F.RSV.ENVS.B1 | CAT TAC CAA GTG AAG TCA GCC TTT G (SEQ ID NO: 28) |
| 1324F.RSV.ENVS.B1 | GTG TCA AAC AAA GGA GTA GAT ACT G (SEQ ID NO: 29) |

The following materials were used in the sequencing reaction: Gel purified DNA samples, Big Dye, Dilution Buffer, Sequencing primers (see tables above) (10 μM each), SAM solution, and BDX beads.

Sequencing mastermix was prepared on ice using per sample volume below:

| | |
|---|---|
| Dilution buffer | 1.5 μl |
| Big Dye v3 | 1 μl |
| Water | 5.5 μl |
| Primer | 1 μl |
| Total | 10 μl (after adding 1 μl of DNA template (~40 ng) |

Nine μl of mastermix were transferred to individual PCR tubes (or skirted 96 well plate), and 1 μl of DNA template was added to appropriate wells. The tubes were placed in the thermocycler, and the reactions were run as follows:

| | | |
|---|---|---|
| Initial denaturation | 96° C. | 2 min |
| PCR 35 cycles | | |
| Denature | 96° C. | 10 sec |
| Anneal | 50° C. | 5 sec |
| Extend | 60° C. | 4 min |
| Storage | 4° C. | indefinite |

Following the PCR reaction, 1.1 mL BDX beads and 5.1 mL SAM solution were combined and periodically vortexed to keep the beads in suspension. Then 55 μl of mixture was dispensed into to each PCR tube. The plate was sealed and shaken for 20 minutes at 4000 RPM. The plate was spun for 2 minutes at 1000 RPM. The sequencing samples were run in an ABI machine using GenSeq software.

Figures 6A, 6B:
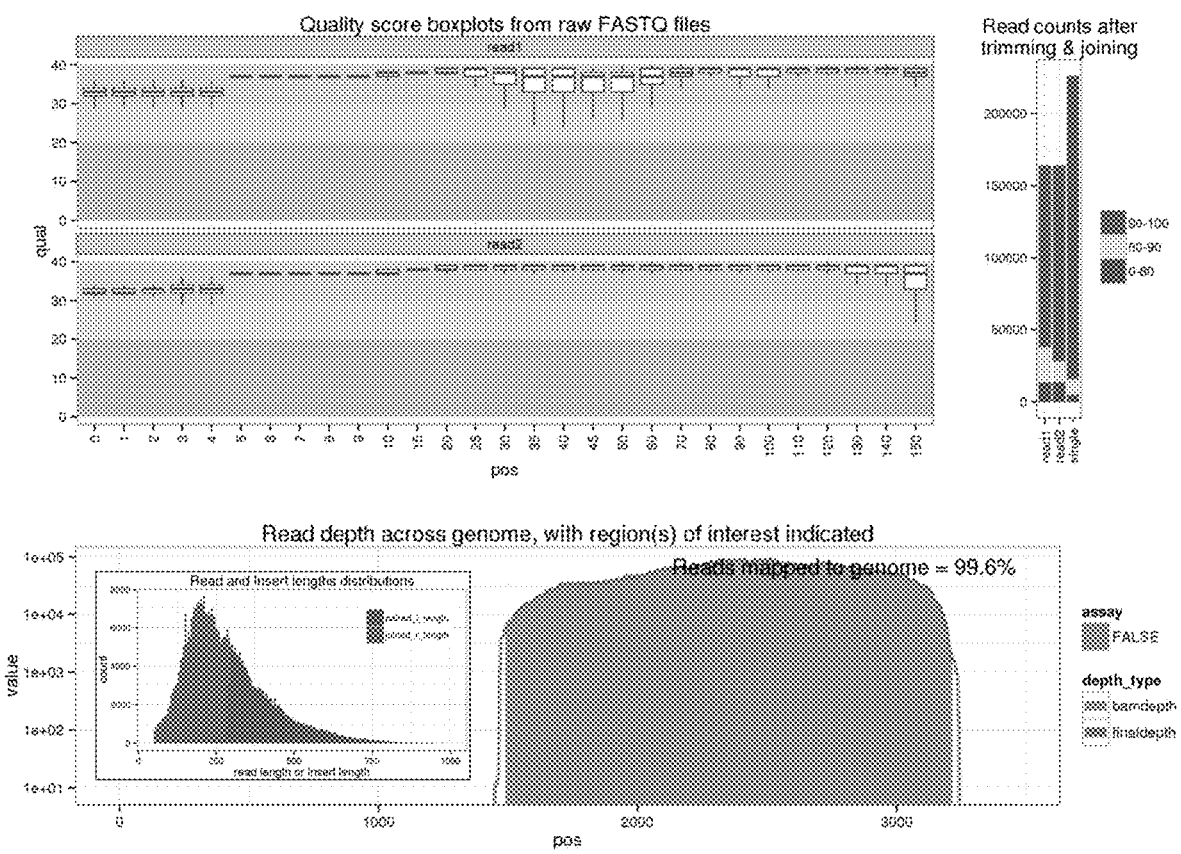
FIG. 6A is a quality control plot for Illumina MiSeq® sequencing of an hRSV isolate, showing that the Q-score is greater than 30 across reads.
FIG. 6B is a quality control plot showing that greater than 99% of reads mapped to the reference genome with evenly distributed read and insert lengths. Minor variants were detected using 3-10% thresholds, with accompanying data on each variant codon, amino acid, and frequency.

Alternatively, the F glycoprotein sequences of cultured hRSV isolates were amplified by RT-PCR, and the samples were subjected to AxyPrep® magnetic PCR purification, Nextera DNA library preparation, and MiSeq® paired end sequencing. Analysis of the reads was performed using a deep sequencing pipeline. FIG. 6A shows a quality control plot for Illumina MiSeq sequencing of an hRSV isolate, showing that the Q-score is greater than 30 across reads. FIG. 6B is a quality control plot showing that greater than 99% of reads mapped to the reference genome with evenly distributed read and insert lengths. Minor variants were detected using 3-10% thresholds, with accompanying data on each variant codon, amino acid, and frequency.

FIG. 7A is a schematic diagram showing the relative locations of the sequencing primers used to sequence the RSV F ORF. FIG. 7B is a neighbor joining tree of the RSV A and RSV B samples tested in the RSV sequencing assay, generated using the sequence data obtained from the sequencing methods above.

SEQUENCE LISTING

The sequence listing was submitted in this patent application on Mar. 8, 2021 as an ASCII text file entitled 1021410_sequence_listing_ST25.txt, which was 10,526 bytes and created on Oct. 25, 2016. The material in the ASCII text file is hereby incorporated by reference.

What is claimed is:

1. A method for simultaneously determining the viral load and genotype of a respiratory syncytial virus (RSV) in a biological sample, comprising:
   a) amplifying a nucleic acid sequence encoding an RSV open reading frame (ORF) in a biological sample using a single set of primers that specifically amplifies an RSV A ORF and/or an RSV B ORF, wherein said single set of primers is a single primer pair, and at least two nucleic acid probes in a quantitative polymerase chain reaction assay, wherein at least one probe specifically binds to an RSV subtype A nucleic acid sequence and at least one probe specifically binds to an RSV subtype B nucleic acid sequence, and wherein the at least two nucleic acid probes are differentially labeled;
   b) amplifying an RSV F ORF in the biological sample with a second single set of primers;
   c) sequencing the RSV F amplification product; and
   d) determining the viral load based on the amount of the amplified nucleic acid sequence produced by the quantitative PCR assay and determining the RSV subtype(s) present in the biological sample based on the binding of at least one probe in step (a), on the sequence determined in step (c), or both.

2. The method of claim 1, wherein amplifying the nucleic acid sequence comprises reverse transcription and real-time PCR amplification.

3. The method of claim 2, wherein reverse transcription and real-time amplification occur in a single step.

4. The method of claim 1, wherein the set of primers amplifies a region of the RSV nucleocapsid (N) protein in RSV A and/or RSV B.

5. The method of claim 1, wherein the set of primers comprises a nucleic acid sequence comprising SEQ ID NO:1 and a nucleic acid sequence comprising SEQ ID NO:2.

6. The method of claim 1, wherein the probe that specifically binds to an RSV subtype A nucleic acid sequence comprises SEQ ID NO:3, and wherein the probe that specifically binds to an RSV subtype B nucleic acid sequence comprises SEQ ID NO:4.

7. The method of claim 1, further comprising a set of primers that amplifies an MS2 region and a nucleic acid probe that specifically binds to a M2 nucleic acid.

8. The method of claim 7, wherein the set of primers comprises a nucleic acid sequence comprising SEQ ID NO:30 and a nucleic acid sequence comprising SEQ ID NO:31.

9. The method of claim 7, wherein the nucleic acid probe that specifically binds to a M2 nucleic acid sequence comprises SEQ ID NO:5.

10. The method of claim 1, wherein the primers and/or probes are labeled with a fluorescent moiety.

11. A method for determining the genotype or viral load of a respiratory syncytial virus (RSV) in a biological sample, comprising:
   a) amplifying a nucleic acid sequence encoding an RSV open reading frame (ORF) in a biological sample using a primer that comprises SEQ ID NO:6 and a primer that comprises SEQ ID NO:7; and
   b) sequencing the amplification product using one or more primers selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19, thereby determining the RSV genotype(s) present or viral load of the RSV in the biological sample.

12. The method of claim 11, wherein amplifying the nucleic acid sequence comprises reverse transcription and real-time PCR amplification, and wherein reverse transcription and real-time amplification occur in a single-step.

13. The method of claim 11, wherein the primers are labeled with a fluorescent moiety.

14. The method of claim 1, wherein the RSV F ORF is amplified with a primer that comprises SEQ ID NO:6 and a primer that comprises SEQ ID NO:7.

15. The method of claim 1, wherein the RSV F ORF amplification product is sequenced using one or more primers selected from the group consisting of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

\* \* \* \* \*